United States Patent [19]
Nierlich et al.

[11] Patent Number: 5,864,052
[45] Date of Patent: Jan. 26, 1999

[54] PROCESS FOR PREPARING ALKYL TERT-BUTYL ETHERS AND DI-N-BUTENE FROM FIELD BUTANES

[75] Inventors: Franz Nierlich, Marl; Paul Olbrich, Haltern; Wilhelm Droste, Marl; Richard Mueller, Marl; Walter Toetsch, Marl, all of Germany

[73] Assignee: Huels Aktiengesellschaft, Marl, Germany

[21] Appl. No.: 899,792

[22] Filed: Jul. 24, 1997

[30] Foreign Application Priority Data

Jul. 24, 1996 [DE] Germany ................. 196 29 904.7

[51] Int. Cl.$^6$ .................................................. C07C 41/06
[52] U.S. Cl. ........................... 568/697; 568/454; 585/809
[58] Field of Search ................. 568/697, 454; 585/809

[56] References Cited

FOREIGN PATENT DOCUMENTS 0 149 698   7/1985   European Pat. Off. .
0 395 857  11/1990   European Pat. Off. .

OTHER PUBLICATIONS

S.T. Bakas et al, "Production of Ethers From Field Butanes and Refinery Streams", Aug. 19–22, 1990, pp. 1–32.
K.H. Walter et al, "The Huels Process for Selective Hydrogentation of Butadiene in Crude C$_4$'s Development and Technical Application", Nov. 11–12, 1993.
R.A. Pogliano et al, "Dehydrogenation–Based Ether Production Adding Value to LPG and Gas Condensate", Mar. 19–21, 1996.
Chauvin A. Hennico et al, "Upgrading of C$_2$, C$_3$, C$_4$ Olefins by IFP Dimersol Technology", Jul./Aug. 1990, pp. 309–315.
G.C. Sturtevant et al, "Selective Production of Light Olefins", 1988 UOP Technology Conference.
Dr. F. Nierlich, "Recent Developments in Olefin Processing for Cleaner Gasoline", Published in Oil Gas Magazine, 1992.
Dr. Nierlich, "Oligomerize for better gasoline", Published in: Hydocarbon Processing, Feb. 1992.
R.L. Espinoza et al, "Catalytic Oligomerization of Ethene Over Nickel–Exchanged Amorphous Silica–Alumina; Effect of The Nickel Concentration", Applied Catalysis, 31 (1987), Elsevier Science Publishers B.V., Amsterdam, pp. 259–266.
W. Grote, "Introducing: Alkar and Butamer", Universal Oil Products Co., Mar. 31, 1958, pp. 73–76.

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

The invention relates to a process for preparing di-n-butene and alkyl tertbutyl ethers in a coupled production from field butanes, which indicates (a) separating the field butanes 1 into n-butane and isobutane in the separation stage 4, (b) dehydrogenating the n-butane 5 in a dehydrogenation stage 6 to give an n-butene-containing dehydrogenation mixture 7, oligomerizing the n-butene in the oligomerization stage 10 to give an oligomer mixture 11 and separating di-n-butene 12 off from this, and (c) de-hydrogenating the isobutane 15 in the dehydrogenation stage 16 to give an isobutene-containing dehydrogenation mixture 17 and reacting the isobutene with an alkanol 20 in the etherification stage 19 to give an alkyl tert-butyl ether 21. In an advantageous embodiment, the field butanes 1, prior to entry into the separation stage 4, are subjected to hydrogenation conditions in the hydrogenation stage 2 and an isomerization stage 3 is assigned to the separation stage 4, by means of which isomerization stage the ratio of n-butane to isobutane is set in accordance with the desired ratio of alkyl tertbutyl ether to di-n-butene.

10 Claims, 1 Drawing Sheet

PROCESS FOR PREPARING ALKYL TERT-BUTYL ETHERS AND DI-N-BUTENE FROM FIELD BUTANES

BACKGROUND OF THE INVENTION

1. Field of the Invention

The invention relates to a process for preparing alkyl tert-butyl ethers (abbreviated as RTBE below, where R represents alkyl) and di-n-butene from field butanes in a coupled production, isobutane being converted into alkyl tert-butyl ether and n-butane being converted into di-n-butene, the ratio of these two products being able to be controlled by setting the ratio of n-butane to isobutane appropriately by isomerization.

2. Background of the Invention

RTBE are used as additives to gasoline to increase the octane rating. They are typically prepared by addition of alkanols to isobutene, which is also termed etherification. The isobutene can originate from four different sources-from steam crackers, propylene oxide plants, petroleum refineries (le. FC crackers) and plants for the dehydrogenation of isobutane (cf. R. A. Pogliano et al., Dehydrogenation-Based Ether Production—Adding Value to LPG and Gas Condensate, 1996 Petrochemical Review, DeWitt & Company, Houston Texas). In the first three sources, the isobutene arises as a constituent of the $C_4$ fraction, that is as a direct byproduct. In the dehydrogenation of isobutane, isobutene is frequently a secondary byproduct of such plants, since the starting material isobutane is likewise obtained as a direct byproduct in steam crackers and petroleum refineries or by isomerization of n-butane, which itself is a byproduct in steam crackers and petroleum refineries. The current world production of RTBE is around 25 million metric t/year, with an increasing trend. The production of butenes and butanes as byproducts in a particular cracker or a particular petroleum refinery is too small to be able to exploit completely the "economies of scale", which are latent in the RTBE process. Therefore, isobutene and/or isobutane (for dehydrogenation) would have to be collected from crackers and/or refineries, in order to be able to operate an RTBE plant at optimum capacity. Alternatively, sufficient $C_4$ fraction could be collected from such plants and these could be worked up on site to isobutene and isobutane. However, opposing both variants, and in particular the second, is the fact that the transport of liquid gases is expensive, not least because of the complex safety precautions.

The term dibutene is applied to the isomeric mixture which, in addition to higher butene oligomers, is formed by dimerization and/or codimerization of butanes, ie. of n-butene and/or isobutene, in the oligomerization of butanes. The term di-n-butene is applied to the dimerization product of n-butene, ie. 1-butene and/or 2-butene. Significant components of the di-n-butene are 3-methyl-2-heptene, 3,4-dimethyl-2-hexene, and, to a minor extent, n-octenes. Di-isobutene is the isomeric mixture which is formed by dimerization of isobutene. Di-isobutene is less highly branched than dibutene and this in turn is more highly branched than di-n-butene.

Dibutene, di-n-butene and di-isobutene are starting materials for preparing isomeric nonanols by hydroformylation and hydrogenation of the $C_9$ aldehydes thus formed. Esters of these nonanols, in particular the phthalic esters, are plasticizers, which are prepared to an important extent and are primarily used for poly(vinyl chloride). Nonanols from di-n-butene are linear to a greater extent than nonanols from dibutene, which in turn are less branched than nonanols from di-isobutene. Esters of nonanols from di-n-butene have application advantages over esters from other nonanols and are therefore particularly in demand.

n-Butene is obtained for the dimerization, just as is isobutene, from $C_4$ fractions, for example, as arise in steam crackers or FC crackers. The $C_4$ fractions are generally worked up by first separating off 1,3-butadiene by a selective scrubbing, e.g. with N-methylpyrrolidone. Isobutene is a desirable and particularly valuable component of the $C_4$ fraction, because it may be chemically reacted, alone or in a mixture with other $C_4$ hydrocarbons, to give sought-after products, e.g. with isobutane to give high-octane isooctane, or with methanol to give methyl tert-butyl ether (MTBE), the most important RTBE. After the reaction of the isobutene, the n-butanes and n-butane and isobutane remain behind. However, the proportion of n-butene in the cracked products of the steam crackers or the petroleum refineries is relatively small. In the case of steam crackers it is in the order of magnitude of barely 10 percent by weight, based on the principal target product ethylene. A steam cracker having the respectable capacity of 600,000 metric t/year of ethylene therefore only delivers around 60,000 metric t/year of n-butene. Although this amount (and that of the isobutenes) could be increased by dehydrogenating the approximately 15,000 metric t/year of n-butane and isobutane, which arise in addition to the n-butanes, this is not advisable however, because dehydrogenation plants require high capital expenditure and are uneconomic for such a small capacity.

Isobutene is, as stated, a sought-after cracking product and is therefore generally not available for the isomerization to n-butene. The amount of n-butanes which a steam cracker or petroleum refinery produces directly is not sufficient, however, to produce sufficient di-n-butene for a nonanol plant of a high enough capacity that it could compete economically with the existing large-scale plants for preparing important plasticizer alcohols, such as 2-ethylhexanol. Propylene oxide plants are, as already stated, less productive still. n-Butanes would therefore have to be collected from various steam crackers, refineries or propyleneoxide plants (or $C_4$ fraction from various sources worked up to n-butene) and the combined n-butene oligomerized in order to cover the dibutene requirement of a sufficiently large economical nonanol plant. However, the transport of liquefied gases is expensive, as already mentioned.

OBJECTS OF THE INVENTION

It would therefore be desirable, and it is an object of the invention to realize, if n-butene and isobutene could be provided at only one site without transport over relatively large distances in amounts as are coupled production for the operation of a large economically advantageous plant for the preparation of di-n-butene, for example having a capacity of 200,000 to 800,000 metric t/year, and the same type of plant for preparing MTBE, e.g. having a capacity of 300,000 to 800,000 metric t/year. It would further be desirable and is an object herein to arrange the link between these plants in such a manner that the ratio of n-butene to isobutene can be set in accordance with the desired amounts of di-n-butene and MTBE.

BRIEF DESCRIPTION OF THE DRAWINGS

A plant which conforms to these requirements is shown with its essential and optional features in FIG. 1 as a block diagram.

DETAILED DESCRIPTION OF THE INVENTION

Figure 1:
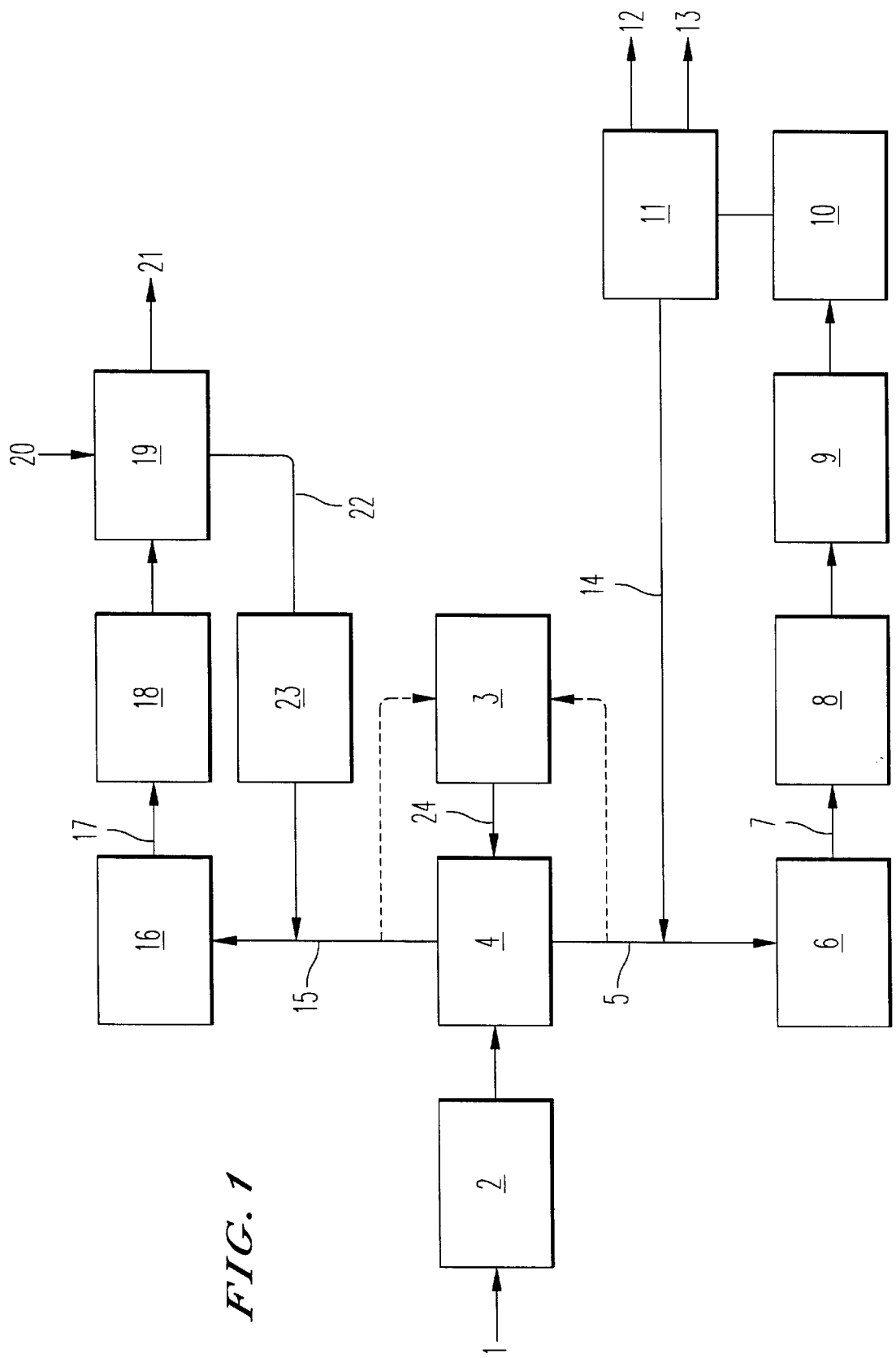

The invention provides a process for preparing di-n-butene and alkyl tert-butyl ethers in a coupled production from field butanes, which comprises (referring to FIG. 1)

(a) optionally dehydrogenating the n-butane and isobutane present in field butanes 1 in a dehydrogenation stage 2, (b) dehydrogenating the n-butane 5 in a dehydrogenation stage 6 to give an n-butene-containing dehydrogenation mixture 7, oligomerizing the n-butene in the oligomerization stage 10 to give an oligomer mixture 11 and separating di-n-butene 12 off from this, and (c) dehydrogenating the isobutane 15 in the dehydrogenation stage 16 to give an isobutene-containing dehydrogenation mixture 17 and reacting the isobutene with an alkanol 20 in the etherification stage 19 to give an alkyl tert-butyl ether 21.

In a preferred embodiment of the process, the field butanes 1, prior to entry into the separation stage 4, are subjected to hydrogenation conditions in the hydrogenation stage 2 and an isomerization stage 3 is assigned to the separation stage 4, by means of which isomerization stage the ratio of n-butane to isobutane can be set in accordance with the desired ratio of di-n-butene to alkyl tert-butyl ether.

The process of the invention is distinguished by high flexibility, since the amounts of di-n-butene and RTBE can be varied in accordance with the market requirements, within the limits which are set by the capacities of the di-n-butene plant and the RTBE plant.

The term field butanes is applied to the $C_4$ fraction of the "moist" portions of natural gas and the gases associated with crude oil, which are separated off in liquid form from the gases by drying and cooling to about $-30°$ C. Low temperature distillation produces therefrom the field butanes, whose composition fluctuates depending on the field, but in which generally about 30% isobutane and about 65% n-butane are present. Other components are generally about 2% $C_{<4}$ hydrocarbons and about 3% $C_{>4}$ hydrocarbons. Field butanes can be used without fractionation as feedstocks in steam crackers or as an additive to motor gasoline. They may be resolved into n-butane and isobutane by fractional distillation. Isobutane is used, for example, to a considerable extent for preparing propylene oxide by cooxidation of propylene and isobutane and as an alkylating agent, by means of which n-butene or isobutene is alkylated to isooctane, which, because of its high octane rating, is valued as an additive to motor gasoline. n-Butane, in contrast, has found fewer important uses. It serves, for example, as butane gas for heating purposes or is used in comparatively small amounts, for example, for preparing polymers or copolymers or maleic anhydride by atmospheric oxidation. Formerly, n-butane was also dehydrogenated via the n-butene stage to give 1,3-butadiene, but this process has become uneconomic in the interim.

Because isobutane is the sought-after component of field butane. n-butane is isomerized on a large scale to give isobutane (cf., for example, R. A. Pogliano et al., Dehydrogenation-based Ether Production, 1996 Petrochemical Review, DeWitt & Company, Houston, Texas, Butamer® Process, page 6- and ST. Bakas, F. Nierlich et al., Production of Ethers from Field Butanes and Refinery Streams. AlChE Summer Meeting, 1990, San Diego, Calif., page 11). It was therefore not part of the technological trend to develop a process which utilizes n-butane as such or even converts isobutane into n-butane in order to prepare more di-n-butene therefrom.

EXAMPLES (Refer to FIG. 1)

(A) Preparation of di-n-butene

Field butane 1 is first separated into n-butane 5 and isobutane 15 in the separation stage 4. This is best carried out in a highly effective column in which n-butane 5 is separated from isobutane 15 by fractional distillation at low temperature or advantageously at elevated pressure, expediently 4 to 7 bar, which isobutane, depending on pressure, boils approximately 10° to 20° C. lower. The $C_{>4}$ hydrocarbons arise as bottom product here, n-butane is taken off in the sidestream and isobutane passes overhead together with lighter ends.

The n-butane 5 is passed into the dehydrogenation stage 6, which is any well known dehydrogenation step. This produces an n-butene-containing dehydrogenation mixture 7. Processes which can be used for this for the dehydrogenation are, for example described by G. C. Sturtevant et al., in Oleflex—Selective Production of Light Olefins, 1988 UOP Technology Conference, and in EP 0 149 698, all incorporated herein by reference. The dehydrogenation is expediently carried out in the gas phase on fixed-bed or fluidized catalysts. e.g. on chromium (III) oxide or advantageously on platinum catalysts having aluminum oxide or zeolites as support. The dehydrogenation generally takes place at temperatures of 400° to 800° C., advantageously 550° to 650° C. Generally, atmospheric pressure is employed, or slightly elevated pressure up to 3 bar. The residence time in the catalyst bed is, depending on catalyst, temperature and sought-after degree of conversion, generally between 1 and 60 minutes. The throughput is accordingly generally between 0.6 and 36 kg of n-butane per $m^3$ of catalyst and per hour.

It is expedient to perform the dehydrogenation only to the point that about 50% of the n-butane remains unchanged in the dehydrogenation mixture 7. Although at a higher temperature higher degrees of conversion can be achieved, cracking reactions then proceed to an increasing extent, which reduce the yield and, owing to coke deposits, decrease the service life of the dehydrogenation catalyst. The optimum combinations of the reaction conditions which lead to the desired degrees of conversion, such as catalyst type, temperature and residence time, may be determined without difficulty by those of ordinary skill in this art.

The dehydrogenation mixture 7 generally contains 90 to 95% $C_4$ hydrocarbons and, in addition, hydrogen and lower- and higher-boiling portions. It is expediently purified prior to oligomerization. In a first purification stage (not depicted in FIG. 1), the $C_4$ fraction and the higher-boiling portions are condensed out. The condensate is distilled under pressure with co-condensed dissolved $C_{<4}$ hydrocarbons passing overhead. In a further distillation, the $C_4$ hydrocarbons are obtained as main product from the bottom product and the relatively small amount of $C_{>4}$ hydrocarbons is obtained as the residue.

The $C_4$ hydrocarbons generally contain small amounts of 1,3-butadiene, such as 0.01 to 5% by volume. It is advisable to remove this component, since, even in markedly smaller amounts, it can damage the oligomerization catalyst. A suitable process is selective hydrogenation 8 which, in addition, increases the proportion of the desired n-butene. A suitable process has been described, for example by F. Nierlich et al. in Erdbl & Kohle. Erdgas, Petrochemie, 1986, pages 73 ff, incorporated herein by reference. It is carried out in the liquid phase using completely dissolved hydrogen in stoichiometric amounts. Suitable selective hydrogenation catalysts are, for example, nickel and, in particular, palladium on a support, e.g. 0.3 percent by weight palladium on activated carbon or, preferably, on aluminum oxide. A small amount of carbon monoxide in the ppm range promotes the selectivity of the hydrogenation of 1,3-butadiene to give the monoolefin and counteract the formation of polymers, the so-called "green oil", which inactivate the catalyst. The process is generally carried out at room temperature or elevated temperature up to 60° C. and at elevated pressures, which are expediently in the range of up to 20 bar. The content of 1,3-butadiene in the dehydrogenation mixture is lowered in this manner to values <1 ppm.

It is further expedient to pass the $C_4$ fraction of the dehydrogenation mixture 7, which is then substantially freed from 1,3-butadiene, through a further purification stage 9, a molecular sieve, prior to the oligomerization stage, as a result of which further substances which are harmful to the oligomerization catalyst are removed and its service life is further increased. These harmful substances include oxygen compounds and sulfur compounds. This purification process has been described by F. Nierlich et al. in EP 0 395 857, incorporated herein by reference. A molecular sieve having a pore diameter of 4 to 15 angstroms, advantageously 7 to 13 angstroms is expediently used. In some cases it is expedient for economic reasons to pass the dehydrogenation mixture successively through molecular sieves having different pore sizes. The process can be carried out in the gas phase, in the liquid phase or in gas liquid phase. The pressure is accordingly generally 1 to 200 bar. Room temperature is expediently employed or elevated temperatures up to 200° C.

The chemical nature of the molecular sieves is less important than their physical properties, ie. in particular the pore size. The most varied types of molecular sieves can therefore be used, both crystalline, natural aluminum silicates, e.g. sheet lattice silicates, and synthetic molecular sieves, e.g. those having a zeolite structure. Zeolites of the A, X and Y type are obtainable, inter alia, from Bayer AG, Dow Chemical Co., Union Carbide Corporation, Laporte Industries Ltd. and Mobil Oil Co.. Also suitable for the process are those synthetic molecular sieves which, in addition to aluminum and silicon, further contain other atoms introduced by cation exchange, such as gallium, indium or lanthanum, or nickel, cobalt, copper, zinc or silver. In addition, synthetic zeolites are suitable in which, in addition to aluminum and silicon, still other atoms, such as boron or phosphorus, have been incorporated into the lattice by mixed precipitation.

As stated above, the selective hydrogenation stage 8 and the purification stage 9 using a molecular sieve are optional, advantageous measures for the process according to the invention. Their order is in principle optional, but the order specified in the Figure is preferred.

The dehydrogenation mixture 7, if appropriate pretreated in the manner described, is passed into the oligomerization stage 10, which is an essential part of the process according to the invention. The oligomerization is carried out in a manner known per se, such as has been described, for example, by F. Nierlich in Oligomerization for Better Gasoline, Hydrocarbon Processing, 1992 (2), pages 45 ff., or by F. Nierlich et al. in the previously mentioned EP 0 395 857 both incorporated herein by reference. The procedure is generally carried out in liquid phase and, as homogeneous catalyst, a system is used, for example, which comprises nickel(ii) octoate, ethylaluminum chloride and a free fatty acid (DE-C 28 55 423 incorporated herein by reference), or, preferably, one of the numerous known fixed-bed catalysts or catalysts suspended in the oligomerization mixture based on nickel and silicon is used. The catalysts frequently additionally contain aluminum. Thus, DD-PS 160 037 (incorporated herein by reference) describes the preparation of a nickel- and aluminum containing precipitated catalyst on silicon dioxide as support material. Other usable catalysts are obtained by exchanging positively charged particles, such as protons or sodium ions, situated on the surface of the support materials for nickel ions. This is successful with the most varied support materials, such as-amorphous aluminum silicate (R. Espinoza et al., Appl. Kat., 31 (1987), pages 259–266; crystalline aluminum silicate (DE-C 20 29 624)-1 zeolites of the ZSM type (Netherlands Patent 8 500 459); an X zeolite (DE-C 23 47 235)1 X and Y zeolites (A. Barth et al., Z. Anorg. Allg. Chem. 521, (1985) pages 207–214); and a mordenite (EP 0 233 302 all incorporated herein by reference).

The oligomerization is expediently carried out, depending on the catalyst, at 20 to 200° C. and at pressures from 1 to 100 bar. The reaction time (or contact time) is generally 5 to 60 minutes. The process parameters, in particular the type of the catalyst, the temperature and the contact time are matched to one another in such a manner that the desired degree of oligomerization is achieved, ie. predominantly a dimerization. In addition, the reaction must obviously not proceed to full conversion, but conversion rates of 30 to 70% per pass are expediently sought after. The optimum combinations of the process parameters may be determined without difficulty by those of ordinary skill.

The residual gases 14 are separated off from the oligomerization mixture 11 and recycled to the dehydrogenation stage 6. If a catalyst of the liquid catalyst type mentioned was used in the oligomerization stage 10 the residual gases 14 should be purified in advance to protect the dehydrogenation catalyst. The oligomerization mixture is initially treated with water, in order to extract the catalyst components. The residual gas separated off is then dried using a suitable molecular sieve, other minor components also being separated off. Polyunsaturated compounds, such as butynes, are then removed by selective hydrogenation, e.g. on palladium catalysts, and finally the residual gas thus purified is recycled into the dehydrogenation stage 6. These purification measures for the residual gas are unnecessary if a solid oligomerization catalyst is used.

Di-n-butene 12 and trimeric n-butene 13, i.e. isomeric dodecenes, are separated off from the remaining liquid phase of the oligomerization mixture 11 by fractional distillation, the di-n-butene, as main product, being directly suitable for preparing nonanols. The dodecenes 13 are a desirable byproduct. They can be hydroformylated, the hydroformylation products can be hydrogenated and the tridecanols thus obtained can be ethoxylated, which produces valuable detergent bases.

(B) Preparation of RTBE (refer to FIG. 1)

The isobutane 15 from the separation stage 4 is passed into the dehydrogenation stage 16 and is there converted to give an isobutene-containing dehydrogenation mixture 17. With respect to the process conditions, this dehydrogenation does not differ substantially from that of the n-butane in the dehydrogenation stage 6. Isobutane is more readily dehydrogenated than n-butane, so that within the range specified in the dehydrogenation stage 6, somewhat milder conditions can be selected on the whole. It is also expedient in this dehydrogenation to seek to attain a conversion rate of only about 50%.

The dehydrogenation mixture 17 contains, as described above for the dehydrogenation mixture 17, in addition to $C_4$ hydrocarbons, hydrogen and lower-boiling components (some of which originate from the field butanes and some of which are formed in the dehydrogenation) and higher-boiling portions, and is expediently purified prior to the etherification. This is performed in turn in a first purification stage (likewise not depicted in the Figure), which corresponds to that which has been described for the purification of the dehydrogenation mixture 7.

The $C_4$ portion of the dehydrogenation mixture 17 thus obtained is expediently passed through a selective hydrogenation stage 18 in which dienes, such as propadiene and 1,3-butadiene, are selectively hydrogenated to monoolefins. The dienes are formed, for example, from propane which had been entrained by the field butanes, from n-butane which had not been completely separated from isobutane in the separation stage 4, or are formed under the dehydrogenation conditions by isomerization and/or cracking reactions. These dienes, at least when the residual gasses 22 are recycled, interfere with the reaction in the dehydrogenation stage 16, less so in the etherification stage 19. The selective hydrogenation stage 18 can therefore alternatively be arranged downstream of the etherification stage 19 in the residual gas stream 22, upstream or downstream of the purification stage 23. This arrangement permits the reactor to be made smaller, if appropriate, because the volume of the residual gas stream 22 is obviously less than that of the dehydrogenation mixture 17. With regard to the process conditions, reference may be made to the explanations in connection with the selective hydrogenation stage 8.

The dehydrogenation mixture 17 is, if appropriate after selective hydrogenation, passed into the etherification stage 19, where the isobutene present therein is reacted with an alkanol 20 in a manner known per se to give an RTBE (see e.g. methyl-tert-butyl ether, Ulimann's Encyclopedia of Industrial Chemistry, Volume A 16, pages 543 ff., VCH Verlagsgesellschaft, Weinhelm incorporated herein by reference). Of the alkanols, preference is given to those having 1 to 6 carbon atoms, for example ethanol, isopropanol, isobutanol and, in particular, methanol. The reaction takes place in the liquid phase or in a gas-liquid phase at a temperature of 50° to 90° C. and at a pressure which is established at the respective temperature. Expediently, a slight excess of alkanol is employed, which increases the selectivity of the reaction of the isobutene and represses its dimerization. The catalyst used is, for example, an acid bentonite or, advantageously, a large-pored acid ion exchanger.

From the etherification stage 19 reaction mixture, the residual gas 22 and, if appropriate, excess alkanol 20 are separated off by distillation from the RTBE 21 formed. In the case of MTBE, the residual gas 22 forms an azeotrope with methanol. The azeotrope is scrubbed with water and separated into an aqueous phase and residual gas 22, which is recycled to the dehydrogenation stage 16, if appropriate via the selective hydrogenation stage 18 (then appropriately arranged in the process sequence) and/or the purification stage 23, the latter again expediently a treatment with a molecular sieve, by which, in particular, oxygen-containing or sulfur-containing impurities are removed which interfere with the dehydrogenation catalyst. At least some of the residual gas 22 can also be recycled to the separation stage 4 (not shown in the Figure), in order to avoid accumulation of n-butane caused by an unsharp n-butene/isobutane separation in the separation stage 4. The aqueous phase which arises in the water scrubbing is worked up to methanol, which is recycled to the etherificaton, and water, which is reused for the scrubbing.

(C) Variation of the amounts of di-n-butene and RTBE

It is expedient to assign an isomerization stage 3 to the separation stage 4, because by this means the ratio of the amounts of di-n-butene and RTBE can be varied. The possibilities for variation are limited only by the capacities of the di-n-butene and RTBE plants. Taking into account the capital expenditure, both plants will certainly rarely be designed to be so large that all of the field butane stream available can be processed in only one of the plants, while the other plant is idle. Nevertheless, the isomerization stage 3 offers the opportunity of reacting flexibly-to the requirements of the market.

If the field butanes 1 contain unsaturated compounds, it is expedient to provide, in addition to the isomerization stage 3, a hydrogenation stage 2 in which these unsaturated compounds are hydrogenated, since they interfere with the isomerization. The hydrogenation is performed in a manner known per se (see, for example, K. H. Walter et al., in The Huls Process for Selective Hydrogenation of Butadiene in Crude $C_4$'s, Development and Technical Application, DGKM Meeting, Kassel, November 1993 incorporated herein by reference). The procedure is expediently therefore carried out in liquid phase and, depending on the catalyst, at room temperature or elevated temperature up to 90° C. and at a pressure of 4 to 20 bar, the partial pressure of the hydrogen being 1 to 15 bar. The catalysts which are customary for the hydrogenation of olefins, e.g. 0.3% palladium on aluminum oxide, are used.

The hydrogenated field butanes 1 are passed into the separation stage 4 and there, as described, separated into n-butane 5 and isobutane 15. If the n/iso ratio is to be altered in accordance with the respective requirement of the two plants, some of the isomer present in excess is drawn off into the isomerization stage 3. The alternative possibilities are indicated in the Figure by dashed lines. In the isomerization stage 3, the isomer drawn off is converted into the other isomer at the most up to equilibrium, which, depending on the temperature, is 40 to 50% n-butane and 45 to 60% isobutane. The isomerization of n-butane and isobutane is a known reaction. The procedure is generally carried out in the gas phase at a temperature of 150° to 230° C., at a pressure of 14 to 30 bar and using a platinum catalyst on aluminum oxide as support, whose selectivity can be further increased by doping with a chlorine compound, such as carbon tetrachloride. A small amount of hydrogen is advantageously added, in order to counteract a dehydrogenation. The selectivity of the isomerization is high. Cracking to form smaller fragments takes place only to a minor extent (approximately 2%) (see for example, H. W. Grote, Oil and Gas Journal, 56 (13), pages 573 ff. (1958) incorporated herein by reference).

The isomerization mixture 24 must be separated into the isomers and for this purpose is expediently passed into the separation stage 4 which is present in any case.

This application is based on German application 196 29 904.7 filed Jul. 24, 1996, incorporated herein by reference.

What is claimed as new and desired to be secured by Letters: Patent of the United Stated is:

1. A process for preparing di-n-butene and an alkyl tert-butyl ether from field butanes, which comprises (a) separating the field butanes into n-butane and isobutane in a separation stage, (b) dehydrogenating the n-butane in a dehydrogenation stage to give an n-butene-containing dehydrogenation mixture, oligomerizing the n-butene in an oligomerization stage to give an oligomer mixture and separating di-n-butene off from this mixture, and (c) dehydrogenating the isobutane in a dehydrogenation stage to give an isobutene-containing dehydrogenation mixture and reacting the isobutene with an alkanol in an etherification stage to give an alkyl tert-butyl ether.

2. The process as claimed in claim 1, wherein the field butanes, prior to entry into the separation stage, are subjected to hydrogenation conditions in a preliminary hydrogenation stage and to isomerization in an isomerization stage wherein the ratio of n-butane to isobutane is changed from that found in said field butanes.

3. The process as claimed in claim 1, wherein a selective hydrogenation and/or a purification stage, in any order, is arranged between the n-butane dehydrogenation stage and the oligomerization stage.

4. The process as claimed in claim 1, wherein residual gasses are separated off from the oligomerization mixture and these residual gasses, optionally after purification, are recycled to the n-butane dehydrogenation stage.

5. The process as claimed in claim 1, wherein a selective hydrogenation stage is arranged between the isobutane dehydrogenation stage and the etherification stage.

6. The process as claimed in claim 1, wherein the residual gasses from the etherification stage are recycled via a purification stage to the isobutane dehydrogenation stage.

7. The process as claimed in claim 1, wherein the alkanol is ethanol, isopropanol, isobutanol or methanol.

8. The process as claimed in claim 1, further comprising preparing a nonanol from said di-n-butene by hydroformylation and hydrogenation of the hydroformylation product.

9. The process of claim 1, further comprising hydroformylation of tri-n-butene (dodecene) obtained from the oligomerization mixture, hydrogenation of the hydroformylation product and ethoxylation of the hydrogenation product to prepare a detergent base.

10. A composition comprising the alkyl tert-butyl ether obtained by the process as claimed in claim 1 and gasoline.

* * * * *